US008413651B2

(12) United States Patent
Powell et al.

(10) Patent No.: US 8,413,651 B2
(45) Date of Patent: Apr. 9, 2013

(54) DISPOSABLE SPACER FOR INHALATION DELIVERY OF AEROSOLIZED DRUGS AND VACCINES

(75) Inventors: Kenneth G. Powell, Raleigh, NC (US); Charles D. Shermer, Raleigh, NC (US); Michael King, Durham, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 12/593,731

(22) PCT Filed: Apr. 7, 2008

(86) PCT No.: PCT/US2008/059529
§ 371 (c)(1),
(2), (4) Date: Feb. 5, 2010

(87) PCT Pub. No.: WO2008/124666
PCT Pub. Date: Oct. 16, 2008

(65) Prior Publication Data
US 2010/0163045 A1    Jul. 1, 2010

Related U.S. Application Data

(60) Provisional application No. 60/910,510, filed on Apr. 6, 2007.

(51) Int. Cl.
*A61M 15/00* (2006.01)
*A61M 16/10* (2006.01)
*A61M 16/00* (2006.01)

(52) U.S. Cl.
USPC .................. 128/203.12; 128/203.15; 604/24

(58) Field of Classification Search ............. 128/203.12, 128/203.15, 200.24, 203.21, 203.29; 604/24
See application file for complete search history.

(56) References Cited

U.S. PATENT DOCUMENTS

| | | | |
|---|---|---|---|
| 4,926,852 | A | 5/1990 | Zoltan |
| 6,098,619 | A | 8/2000 | Britto |
| 6,202,643 | B1 | 3/2001 | Slader |
| 6,550,473 | B1 | 4/2003 | Slader |
| 6,679,252 | B2 | 1/2004 | Slader |
| 2002/0092521 | A1 | 7/2002 | Sullivan |
| 2003/0226562 | A1* | 12/2003 | Schmidt et al. .......... 128/200.24 |
| 2008/0035143 | A1* | 2/2008 | Sievers et al. ............ 128/203.12 |

* cited by examiner

*Primary Examiner* — Nicholas Lucchesi
*Assistant Examiner* — Leah Stohr
(74) *Attorney, Agent, or Firm* — Robert E. West

(57) ABSTRACT

A device, system and method is provided for dispersing an aerosol formulation comprising a medicament. The device may be useful in administering inhaleable vaccines and the like. The device designed for low cost and applicability to a multitude of patient populations. The device has a spacer (10) is suitable for use with a wide range of aerosolized formulations, particularly powders. The spacer (10) may be an expandable volume spacer (10). The spacer (10) may also be used with other inhalation aids (80). The spacer (10) may include a multi-purpose outlet (40) for use with different groups within the target patient population.

14 Claims, 18 Drawing Sheets

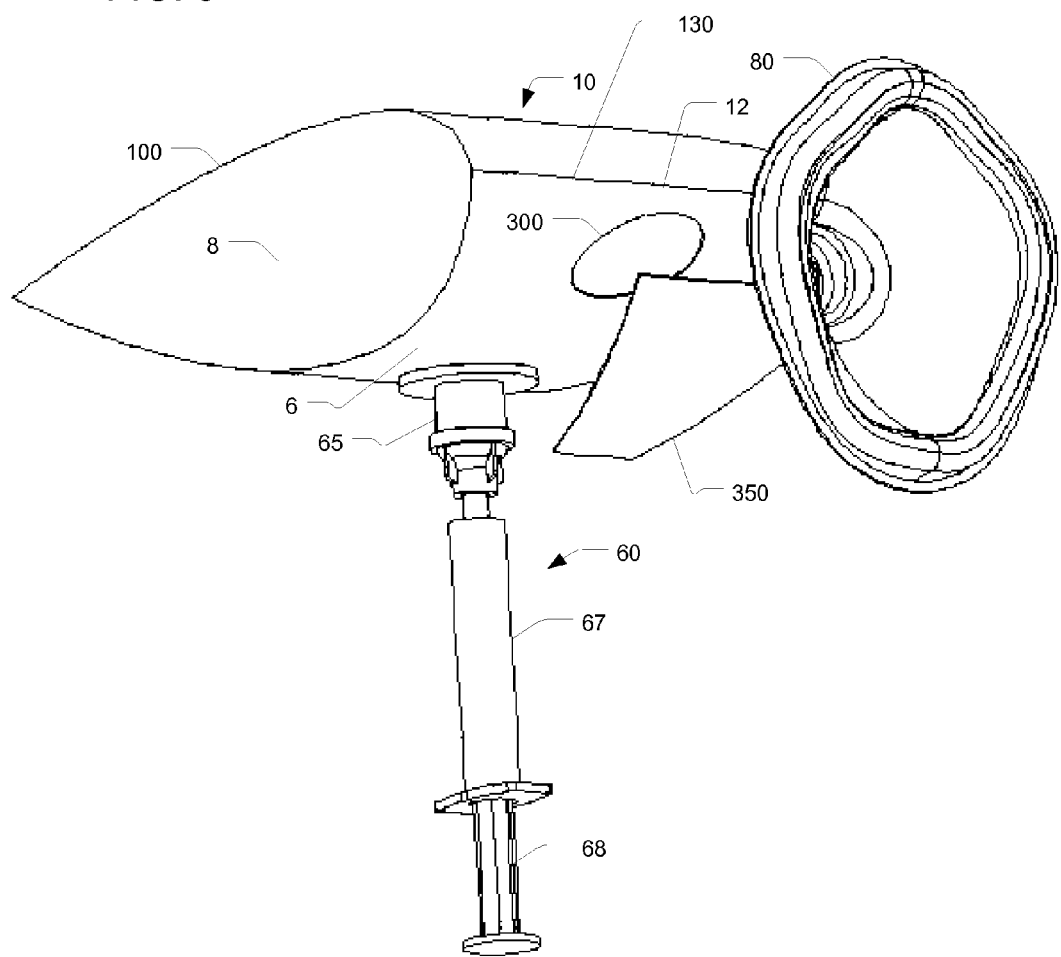

DISPOSABLE SPACER FOR INHALATION DELIVERY OF AEROSOLIZED DRUGS AND VACCINES

RELATED APPLICATIONS

This application claims priority to U.S. Provisional Patent Application No. 60/910,510 filed Apr. 6, 2007, which is hereby incorporated by reference in its entirety.

FIELD OF THE INVENTION

The present invention relates to devices for delivering aerosolized drugs and vaccines, including but not limited to spray-dried measles vaccine formulations.

BACKGROUND OF THE INVENTION

Historically, measles vaccination campaigns using a live, attenuated vaccine have been very effective and are attributed to an 85% reduction in measles mortality since the 1980's. While the syringes used in these campaigns have been demonstrated to be safe and effective, their use poses logistical issues centered on proper disposal. Aerosol delivery has been intensively investigated and recently has been quite successful. Currently, the World Health Organization (WHO) recommends that optimal vaccination to control measles outbreaks should occur in children at nine months of age.

Historically, respiratory delivery was accomplished using a small nebulizer based on reconstitution of the lyophilized Edmonston-Zagreb strain of the measles vaccine otherwise used for injection. This strategy has worked well and is generally referred to as the Classic Mexican Device or CMD. However, since these nebulizers use compressed air, a power supply is necessary and thus the delivery system does not lend itself to use in the more remote regions of the world. Additionally, there is tremendous vaccine waste due to the dead volume in the nebulizers, the inefficient utilization of the mist generated and to the very low room temperature stability of the reconstituted vaccine.

Recent developments in aerosol delivery include "rupturable membranes" technology. In these types of devices, a syringe without an injection needle is used as the means to pressurize the device and burst the films that define the ends of a capsule containing the vaccine, thereby expelling the dose for delivery. They are single use, disposable and contain no sharps. Published patent applications and issued patents related to these types of devices include the following:

Published US Patent Applications US 2005/0000514, US 2004/0163645, US 2004/0079363, US 2004/0011356, US 2003/0047184, US 2002/0092524, US 2002/0092523, US 2002/0092521, and US 2002/0092520. Additionally, U.S. Pat. Nos. 6,929,005; 6,782,887; 6,722,364; 6,644,309; and 6,443,152 describe this technology. These patents are incorporated by reference herein in their entirety.

The above-described technology is predicated on the ability of the patient to coordinate his or her breathing with the actuation of the device. However, young children, typically those under four years of age, are generally incapable of this timing. Furthermore, it may not be possible to communicate the need for timing to the patent.

Thus alleviation of the timing issue has been solved by providing a fixed volume chamber between the medicament delivery device and the patient, however, a problem of the conventional fixed volume chamber devices are far too expensive to be considered disposable, and/or they are not at all collapsible or are insufficiently collapsible to be carried conveniently in a briefcase, vest pocket, or the like. U.S. Pat. Nos. 4,637,528 and 4,641,644 disclose aerosol inhalation devices that are partly collapsible, but not to a generally thin, flat configuration. U.S. Pat. No. 4,953,545 discloses a chamber that is disposable but not collapsible. U.S. Pat. Nos. 6,202, 643 and 6,550,473 describe a collapsible device; however, its integrated valve makes it an expensive device to manufacture. Furthermore, each of the device designs described in the patents above must be tailored to the target patient population. Therefore, a multitude of devices is needed to cover an entire patient population.

The retail cost of conventional chamber devices described above typically is as much as nearly $20.00 and some are as high as $60.00. This cost may be acceptable to patients having chronic conditions which buy a device that is tailor made to their usage, however, many patients need inhaler medications for only a short period of time, or only a single use as in the case of mass vaccinations, in which case the high cost of conventional chambers is very unsatisfactory, especially if a substantially lower cost alternative were available. Additionally, a costly inventory of multiple device designs would be needed with these devices such that various configurations are available for each patient type.

What is needed is a device and or method to aid in coordination of delivery and inhalation to patients of all ages. Additionally, it would be of benefit to have a single device which accomplishes this objective for the entire population of users.

DESCRIPTION OF THE INVENTION

To enhance the effectiveness of medicament delivery devices, and to address the inability of young children to coordinate their breathing with the actuation of inhalation devices, one aspect of the present invention provides an additional component referred to herein as a "spacer." The spacer is an accessory that may be used with inhalation devices such as the devices described above to enhance the amount of aerosolized formulation made available to the patient. Aerosolized formulations are prone to dispersing or settling quickly in open air. A spacer having characteristics of the present invention create a controlled volume in which the formulation is contained and can have a "residence time" after it is expelled from the delivery device (e.g. MDI, pMDI). The spacer effectively acts as a "holding chamber" to contain the medicament and decouple inspiration from actuation of the device. This enables the patient to inhale the medicament formulation over several respirations and maximize the therapeutic benefit. Preferably, a spacer having aspects of the invention facilitates low cost developing world vaccination campaigns.

In a preferred embodiment of the invention, a "spacer" or "holding chamber" has integral features and design that allow it to be used for either an adult or pediatric patient. In other designs three or more patient populations are served by a single device having aspects of the invention. In use of the device, a determination may be made at the point of care by the health care worker who will administer the drug or vaccine formulation as to the type of use required, and the device preferably has features to accommodate both types of usage. It could be of benefit to have an adaptable device as this reduces inventory and simplifies field logistics.

In a preferred embodiment of a device having aspects of the invention, the spacer is a disposable, single patient use, single unit dose delivery component. Furthermore, in a preferred embodiment of a device having aspects of the invention, the spacer functions without any internal valving system to control the patient's inhalation/exhalation airflow, thus making it less complex, easier to manufacture, and more cost effective. Alternatively, a device having aspects of the invention may incorporate a low-cost valved design described herein.

In a preferred embodiment of a device having aspects of the invention, the spacer material is selected for easy disposal worldwide (i.e. incineration, biodegradable). Preferably, the spacer is paper-based, which provides a very low cost base, can be fabricated in high volumes, folds flat, has intrinsically low triboelectric effects, and can be coated with a wide assortment of surface modifiers. A preferable material is SBS whiteboard, which is thin but sufficiently rigid, folds easily and is low cost. Alternatively, the spacer could be made from plastic sheeting (e.g. polypropylene, polyethylene) or could be molded plastic (e.g. injection molded or blow molded). Spacers fabricated from a SBS whiteboard cardstock or similar material could have the surfaces of the cardstock pre-cut, scored, perforated and glued together so that the spacer can be folded flat or nested together in a stackable arrangement that minimizes the overall size for bulk packaging or kitting with other delivery devices and accessories. Prior to use, the spacer is manipulated into a 3D shape to create an enclosed volume.

In one embodiment of a device having aspects of the invention, the spacer is designed to fold flat and become substantially sheet-like or be stackable (i.e. nesting features, or conforming external geometries) to minimize overall size for bulk packaging or kitting with other device components. In embodiments which fold substantially flat for storage, at the time of use, the spacer is "popped" into a three-dimensional shape to create an enclosed volume into which an aerosol formulation can be dispersed. The formulation delivery device then may be connected to the bottom or top of the spacer. In other embodiments, the medication delivery device is pre-attached to the spacer.

In one embodiment of a device having aspects of the invention, on either end of the spacer, there are "vented" openings that are covered by a porous breathable material.

In a preferred embodiment of a device having aspects of the invention, the device is fabricated using materials for minimum cost but still meet functional performance criteria, safety and efficacy requirements. Potential applications are the delivery of prophylactic single dose vaccines or the rapid delivery of medications to a mass population.

In a preferred embodiment of the invention, the device is for dispersing an aerosol formulation comprising a powdered medicament. The spacer is suitable for use with a wide range of aerosolized formulations, particularly powders. With these types of medicament delivery devices, a powder formulation is filled into a cylindrical capsule, which has heat-sealed films on both ends. The capsule is retained in a housing that is designed to mate to the spacer. A syringe is attached to the capsule. When the syringe is stroked closed, sufficient pressure is generated on the capsule film to burst the films and the powder formulation is expelled from the capsule, through the port, into the spacer, and is made available to the patient for inhalation via an outlet. In one embodiment of the invention the outlet is a multi-purpose outlet for use with different groups within the target patient population. The devices having aspects of the invention may be used in self administration of medicaments or in administration by another inter alia a caregiver or nurse.

In one embodiment having aspects of the invention, a multi-use outlet is provided. Depending on the patient that is intended to use the spacer, the appropriate port of the spacer is prepared by a manipulation of the device by the care-giver. In one embodiment, peeling away a vent and exposing a different shaped port opening in the spacer accomplishes this task. In another embodiment, folding away a movable portion of the spacer and exposing a different shaped port opening in the spacer accomplishes this task. In another embodiment, a perforated portion of the spacer is removed, which exposes a different shaped port opening in the spacer accomplishes this task. In the embodiments which utilize a vent, the vent is made of a porous, breathable material such as a surgical drape, filter material, or similar non-woven material. The vent is preferably attached to the spacer with a double-sided medical grade adhesive that is designed to have the stronger adhesive layer on the vent side so that when it is peeled away no adhesive residue is left behind on the spacer. Generally, the two modes of operation of the outlet are adult, and pediatric; however outlets may be designed for a multitude of applications such as: connection to a ventilator, connection to mask, etc. Additionally, even though the embodiments described herein describe two modes of operation for the outlet, it would be within the scope of the invention to provide three or greater modes. Generally, in use of the device for an adult patient, the pre-cut outlet acts as a mouthpiece feature on the spacer, with no additional parts or manipulations required. The adult patient puts his/her mouth over the opening in the spacer and inhales to receive the dose. Generally, for a pediatric patient, larger openings which are adapted to receive a mask or are configured to be mask-like are required. In this mode, the opening is manipulated such that an opening adapted to receive a mask or a mask-like feature on the spacer is formed. The mask is preferably flexible and form fitting to accommodate a wide range of face shapes and sizes. The mask is preferably made from a formed non-woven material, thermoformed plastic, or formed paper stock. The material may also be an easily biodegradable plastic that degrades in water or sunlight such as PLA (polylactic acid which is synthesized from processed corn). The mask is preferably designed to attach to the spacer by an interference fit, or having undercut features in the mask that mate to a similar feature on the spacer so that it can be securely attached. Other attachments known in the art would be of use here. Preferably, the mask is designed so that it can be nested or stacked in bulk quantities to reduce overall shipping size. The mask is placed over the patient's nose and mouth and the patient inhales to receive the dose. With the device in position in the mouth of the adult patient or with the mask over the face of the pediatric patient, the aerosol delivery system is activated. A plume of dispersed aerosol is introduced into the spacer and is made equally available to either end of the spacer.

In embodiments which utilize a mask, a mask made from a thermoformed plastic or similar material may comprise an integral valve system made of flexible films to control or divert the patient's breathing in and out of the spacer. Preferably, the valves are pre-cut thin films that are mounted along one edge and act as door. As the patient inhales, the inlet valve (preferably located in the center of the mask) opens toward the patient and the aerosolized formulation is drawn from the spacer, through the open valve and into the patient's pulmonary tract. As the patient exhales, the inlet valve is forced closed and the outlet valve (preferably located at the bottom perimeter of the mask) opens. This combination of valves minimizes the patient's exhalation from entering the spacer and possibly degrading the aerosolized formulation. An alternate embodiment of the invention comprises an integral mask and spacer configuration. In this embodiment, the mask has a portion which acts as a low volume spacer and in some situations may be better suited to specific patient breathing patterns to achieve effective dose delivery.

In one embodiment of a spacer having aspects of the invention, internal features are minimized. The ability to minimize and/or eliminate internal features such as valves, baffles, etc.

("internals") in the spacer offers additional opportunities for cost reduction and improved shipping and use logistics. Since the powder emitted from medicament devices described above move at fairly high velocities, an initial concern was that a baffle or some other feature would be necessary to reduce deposition on the face of the patient during use, because deposition to the face reduces the dose available for inhalation. However, in side by side testing using different spacer designs of the invention with anatomical breathing models, it was determined that powder loss due to facial deposition was less than three percent. It is hypothesized that the powder that strikes the face is predominantly larger, non-respirable particles that have higher momentum due to their greater mass and would not be expected to be efficacious for respiratory delivery anyway. Additionally, because deposition on the face is partly compensated for by a decrease in powder "lost" to deposition that would occur on any internals in the spacer, powder loss on the face was judged insignificant.

According to further embodiments of the present invention, a method for administering a medicament to a user includes providing a medicament delivery device and a spacer including: an inlet, at least one outlet and a port. The medicament delivery device is actuated to generate a plume within the chamber, whereupon the medicament is inhaled, preferably mixed with external air to carry the medicament through the exit port, into the patient.

Any of a variety of therapeutic or prophylactic agents can be used in the methods and devices of the invention. A "therapeutic agent" (sometimes referred to herein as a "medicament"), as used herein, means an agent that can elicit a therapeutic effect in a cell, tissue, organ or patient to which it is administered. Compositions that comprise one or more therapeutic agents can produce a "clinically efficacious result" when administered to a patient. As used herein, the term a "clinically efficacious result" means a clinically useful biological response, and applies both to diagnostic, prophylactic and therapeutic uses. The therapeutic agents can be any of a variety of types, including, e.g., polypeptides (proteins), polynucleotides (nucleic acids), small molecules such as steroids and viral particles. The terms polypeptide and protein are used interchangeably herein, as are the terms polynucleotide and nucleic acid. Suitable polypeptides or peptides include, but are not limited to, growth factors, cytokines, antigens, antibodies, interleukins, lymphokines, interferons, enzymes, etc., including, but not limited to, anti-IgE antibodies, tissue plasminogen activator (tPA), calcitonin, erythropoeitin (EPO), factor IX, granulocyte colony stimulating factor (G-CSF), granulocyte macrophage colony stimulating factor (GM-CSF), growth hormone (particularly human growth hormone), heparin (including low molecular weight heparin), insulin, insulin-like growth factors I (IGF-I) and II (IGF-II), Glucagon Like Proteins (GLP), interleukins, interferons, luteinizing hormone releasing hormone, somatostatin and analogs, vasopressin and analogs, follicle stimulating hormone, amylin, ciliary neurotrophic factor, growth hormone releasing factor, insulinotropin, macrophage colony stimulating factor(M-CSF), nerve growth factor, parathryoid-hormone, antitrypsin, anti-RSV antibody, DNase, Her2, CFTR (cystic fibrosis transmembrane conductance regulator gene product, useful to treat cystic fibrosis), insulin, etc. In a preferred embodiment, the polypeptide is insulin. Polypeptides such as marker proteins can also be used. In a preferred embodiment, the polypeptides are found within or on the surface of infectious agents, such as bacteria, viruses, protozoan or other parasites, including malaria, or the like, or as a recombinantly produced protein or polypeptide that mimics the biological activity of a toxin produced by a bacteria. Such polypeptides can serve as immunogenic agents, for use, e.g., in a vaccine. The polypeptide can be a naturally occurring one or it can be produced recombinantly. Polypeptides used in the invention can be fragments of full-length proteins. Any desirable size (length) polypeptide can be used. For example, a peptide that comprises one or more epitopes and/or antigenic sequences can serve as an agent to elicit an immune response. Suitable polynucleotides include, e.g., vectors comprising recombinant sequences that encode therapeutic polypeptides of interest. These polynucleotides can any encode any of the therapeutic polypeptides noted above, or others. Suitable virus particles include, e.g., partially or fully inactivated viral particles that can serve as antigens for vaccines, such as, e.g., measles influenza, RSV and polioviruses. In a preferred embodiment, the virus is inactivated influenza virus. Typical strains of influenza include, e.g., A/PR/8/34 and the Port Chalmers strain. Subunit vaccines, prepared by conventional methods, are also included. In another embodiment, conventional viral vectors that are suitable for inhalation administration, including but not limited to adenovirus-based vectors or AAV-based vectors, comprising one or more genes that encode therapeutic proteins, are included. Any suitable immunogen as defined herein may be employed. The immunogen may be a viral immunogen. The immunogen may therefore be derived from members of the families Picornaviridae (e.g. polioviruses, etc.); Caliciviridae; Togaviridae (e.g., rubella virus, dengue virus, etc.); Flaviviridae; Coronaviridae; Reoviridae; Birnaviridae; Rhabodoviridae (e.g. rabies virus, etc.); Filoviridae; Paramyxoviridae (e.g. mumps virus, measles virus, respiratory syncytial virus, etc.); Orthomyxoviridae (e.g. influenza virus types A, B and C, etc.); Bunyaviridae; Arenaviridae; Retroviradae (e.g. HTLV-I; HTLV-II; HIV-1 and HIV-2); and simian immunodeficiency virus (SIV) among others. Alternatively, viral immunogens may be derived from papillomavirus (e.g. HPV); a herpesvirus; a hepatitis virus, e.g. hepatitis A virus (HAV), hepatitis B virus (HBV), hepatitis C (HCV), the delta hepatitis virus (HDV), hepatitis E virus (HEV) or hepatitis G virus (HGV); and the tick-borne encephalitis viruses. Bacterial immunogens for use in the invention can be derived from organisms that cause anthrax, botulism, plague, diphtheria, cholera, tuberculosis, tetanus, pertussis, meningitis and other pathogenic states, including, e.g., Meningococcus A, B and C, *Haemophilus* influenza type B (HIB), *Helicobacter pylon, Vibrio cholerae, Escherichia coli, Campylobacter, Shigella, Salmonella, Streptococcus* sp., *Staphylococcus* sp, *Clostridium botulinum, Bacillus anthracis,* and *Yersinia pestis.* Furthermore, the device and method may utilize a combination of bacterial immunogens which is provided in a single composition comprising, for example, diphtheria, pertussis and tetanus immunogens. Suitable pertussis immunogens are pertussis toxin and/or filamentous haemagglutinin and/or pertactin, alternatively termed P69. An anti-parasitic immunogen may be derived from organisms causing malaria and Lyme disease. In certain aspects of the invention, the bacterial immunogen is selected from the group consisting of recombinant *Staphylococcus* enterotoxin B (rSEB), *Bacillus anthracis* recombinant Protective Antigen (rPA), recombinant *Clostridium botulinum* neurotoxin, and *Yersinia pestis* F1V fusion protein. In particular embodiments, combinations of the above immunogens are utilized in the practice of the invention to produce multivalent vaccines for inhalation. Any suitable therapeutic gene can be used, including, e.g., genes suitable for treatment of cystic fibrosis. Suitable steroids include, e.g., conventional steroids for treating asthma, bronchial spasms, or other conditions, which are well known to those of skill in the art.

Objects of the present invention will be appreciated by those of ordinary skill in the art from a reading of the figures and the detailed description of the preferred embodiments which follow, such description being merely illustrative of the present invention. All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

BRIEF DESCRIPTION OF THE DRAWINGS

The accompanying drawings, which are incorporated in and constitute a part of the specification, illustrate embodiments of the invention and, together with the description, serve to explain principles of the invention.

FIG. 3 shows a perspective view of the embodiment of the design of FIG. 1 for a different patient population.

FIGS. 16A' and 16B' show a shaded view of a distal perspective and proximal perspective views, respectively, of the mask of the embodiment of FIG. 13A.

DETAILED DESCRIPTION OF THE PREFERRED EMBODIMENTS

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. In the figures, certain components and the thicknesses of some layers may be exaggerated for clarity.

Figure 1:
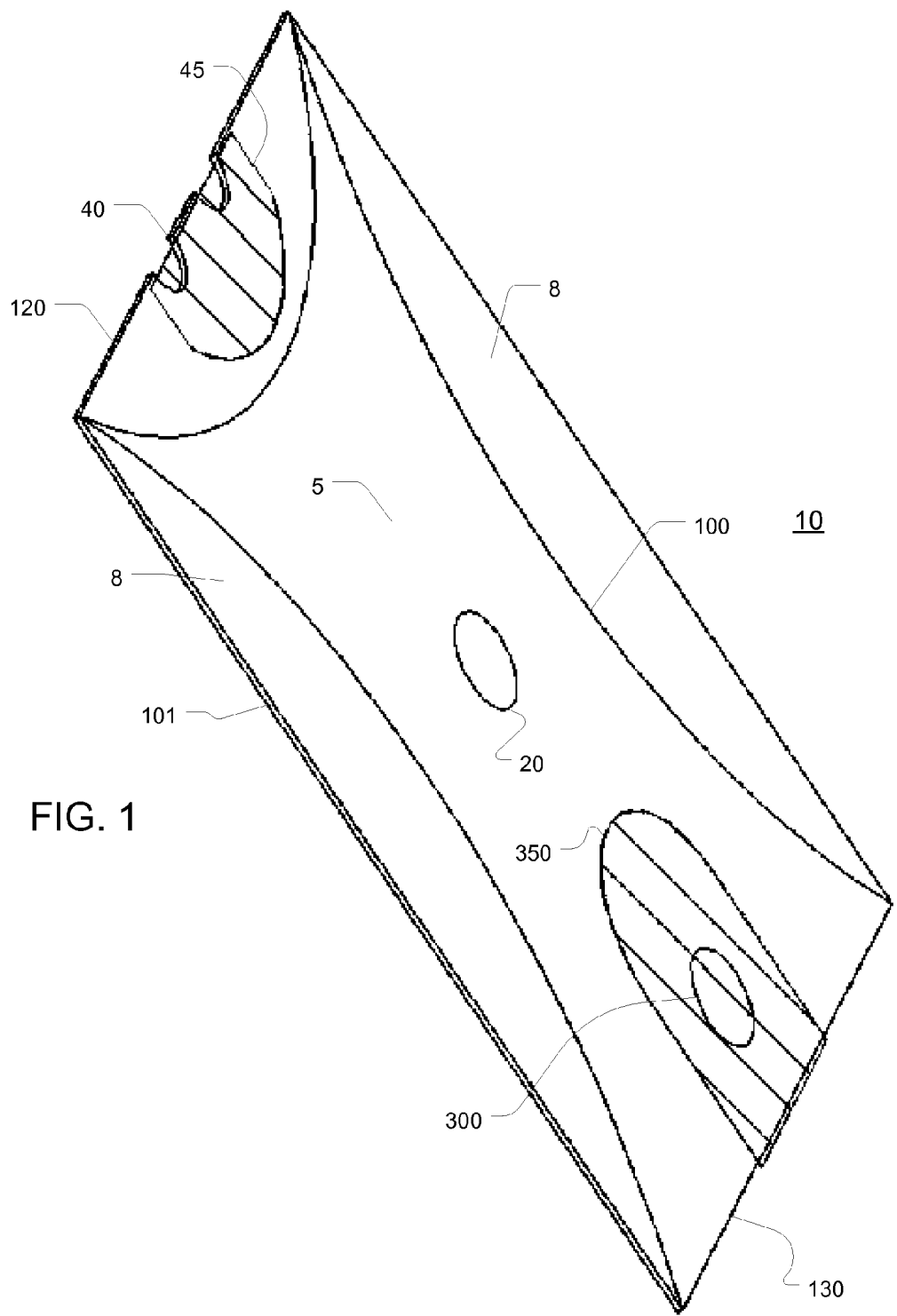
FIG. 1 shows an embodiment having aspects of the invention in a perspective view, with the spacer in flattened state.
Figure 2A:
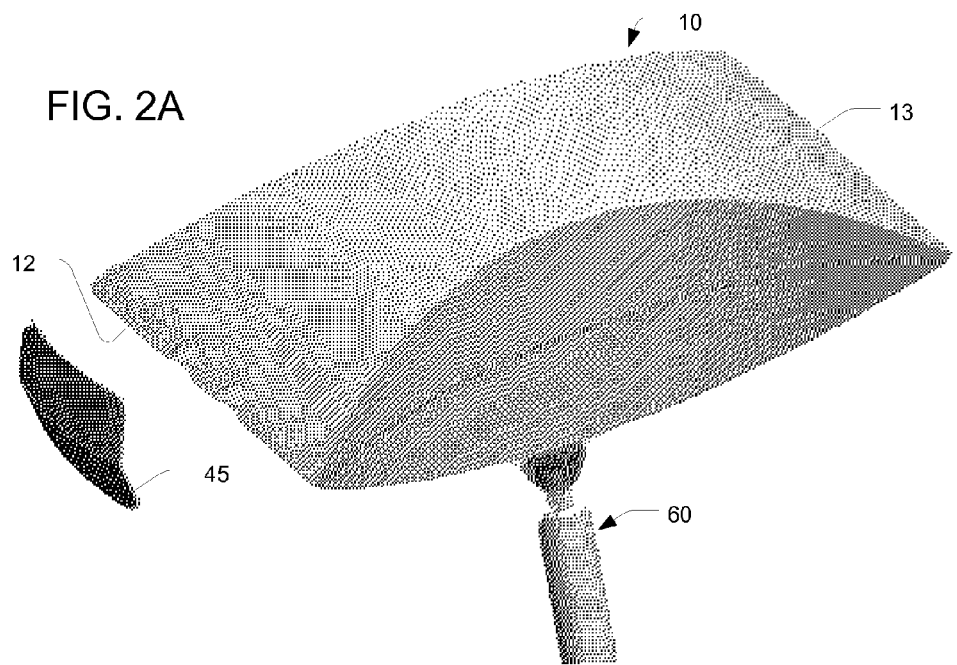
FIGS. 2A and 2B shows a shaded view and wireframe view, respectively, of the embodiment of FIG. 1 in an expanded state.
Figure 2B:
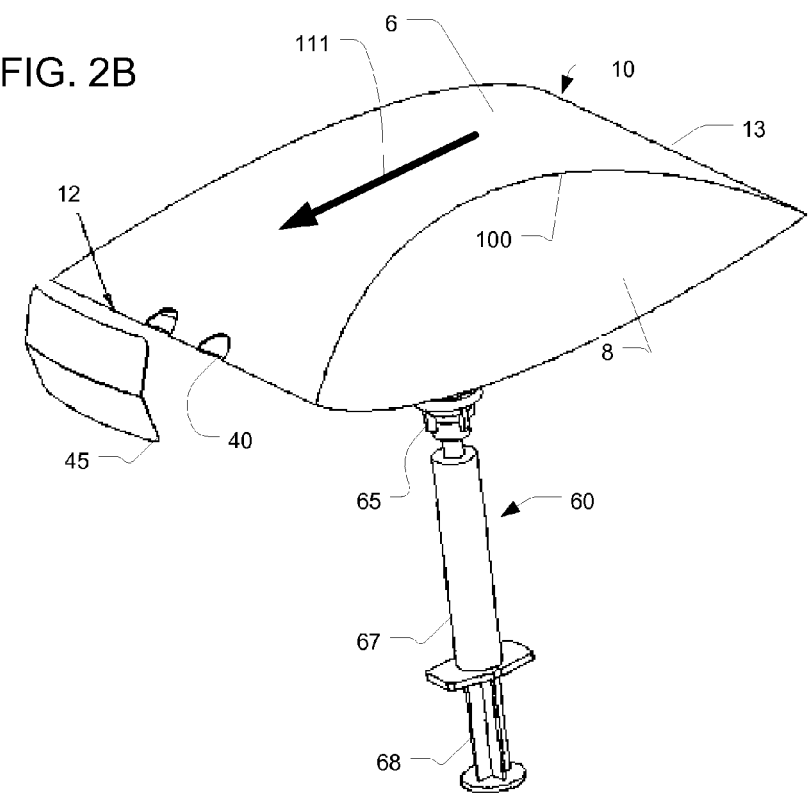

Now turn to FIG. 1, which shows an embodiment of a spacer 10 in flattened state having a top surface 5, a bottom surface 6, and an inlet 20. Spacer further includes a first end 120, and a second end 130. Spacer 10 has a flattened state shown in FIG. 1, and an expanded state (shown in FIGS. 2A/B-3). In this embodiment inlet 20 is disposed on the top surface of the spacer, however, it could be placed on the bottom surface 6 or another surface formed when spacer 10 is expanded. The inlet 20 is adapted to receive a medication delivery device, preferably an inhalation medicament delivery device, more preferably a powdered medicament delivery device. Preferably inlet 20 is adapted to mate correspondingly to the medicament delivery device such that a substantially sealed connection is made between spacer 10 and the medicament delivery device. Additionally, structural crease 100 is in an arcuate path from first end 120 of the spacer 10 to second end 130. Structural crease 100 serves to hold spacer 10 in an expanded state by the manipulation of sides 8, and its interaction with fold 101. Various dimensional and structural changes to structural creases and folds can serve to accomplish the desired effect of creating an expandable flattened structure, which converts from substantially two dimensional to substantially three dimensional.

First end 120 of Spacer 10 further includes at least one outlet 40 which is configured to be suitable for use by a first patient population. In this embodiment outlet 40 is for an adult patient. Outlet 40 is preferably covered by vent cover 45. Preferably vent 40 and vent cover 45 allow airflow into the spacer as the patient inhales and draws the aerosolized formulation into their pulmonary tract. Vent cover 45 is preferably a porous breathable material and is preferably attached to the spacer by a semi-permanent peelable medical grade adhesive material. In an alternate embodiment vent cover 45 is non-permeable and blocks any airflow, and in this case airflow is provided into spacer by other means.

Second end 130 of Spacer 10 further includes at least one orifice 300 which is configured to be suitable for use by a second patient population. In this embodiment orifice 300 is adapted for use in conjunction with a mask for a pediatric patient. Orifice 300 is preferably covered by cover 350. Preferably orifice 300 and cover 350 allow airflow into the spacer as the patient inhales and draws the aerosolized formulation into their pulmonary tract. Cover 350 is preferably a porous breathable material and is preferably attached to the spacer by a semi-permanent peelable medical grade adhesive material. In an alternate embodiment cover 350 is non-permeable and blocks any airflow, and in this case airflow is provided into spacer by other means.

The use of this embodiment for a first population is shown in FIGS. 2A-2B where First end 120 becomes the distal end 12 of the device. "Distal" is defined as the portion of spacer 10 closest to the patient's face. Spacer 10 is manipulated into an expanded state. Medication delivery device 60 having capsule 65 and capsule outlet 66 is engaged to port 20 of spacer 10. Vent cover 45 is removed from spacer 10 and the patient places their mouth substantially over outlet 40. The patent then activates the medication delivery device 60, which in this case involves depressing plunger 68. Medicament discharged from medication delivery device 60 into spacer 10 via port 20. The cover 350 over orifice 300 by means of its design does not allow medication to escape. The patient then inhales and preferably orifice 300 becomes an inlet vent and allows the flow of air external to spacer 10 to enter the interior of spacer 10 and through the permeable cover 350, if present, and mix with the medicament to flow through outlet 40 into the patient. Arrow 111 represents the general direction of the airflow during inhalation. Preferably the patient accomplishes a full dose delivery in a single breath; however, it is not outside of the scope of the invention to perform multiple breaths utilizing the spacer.

Figure 4:
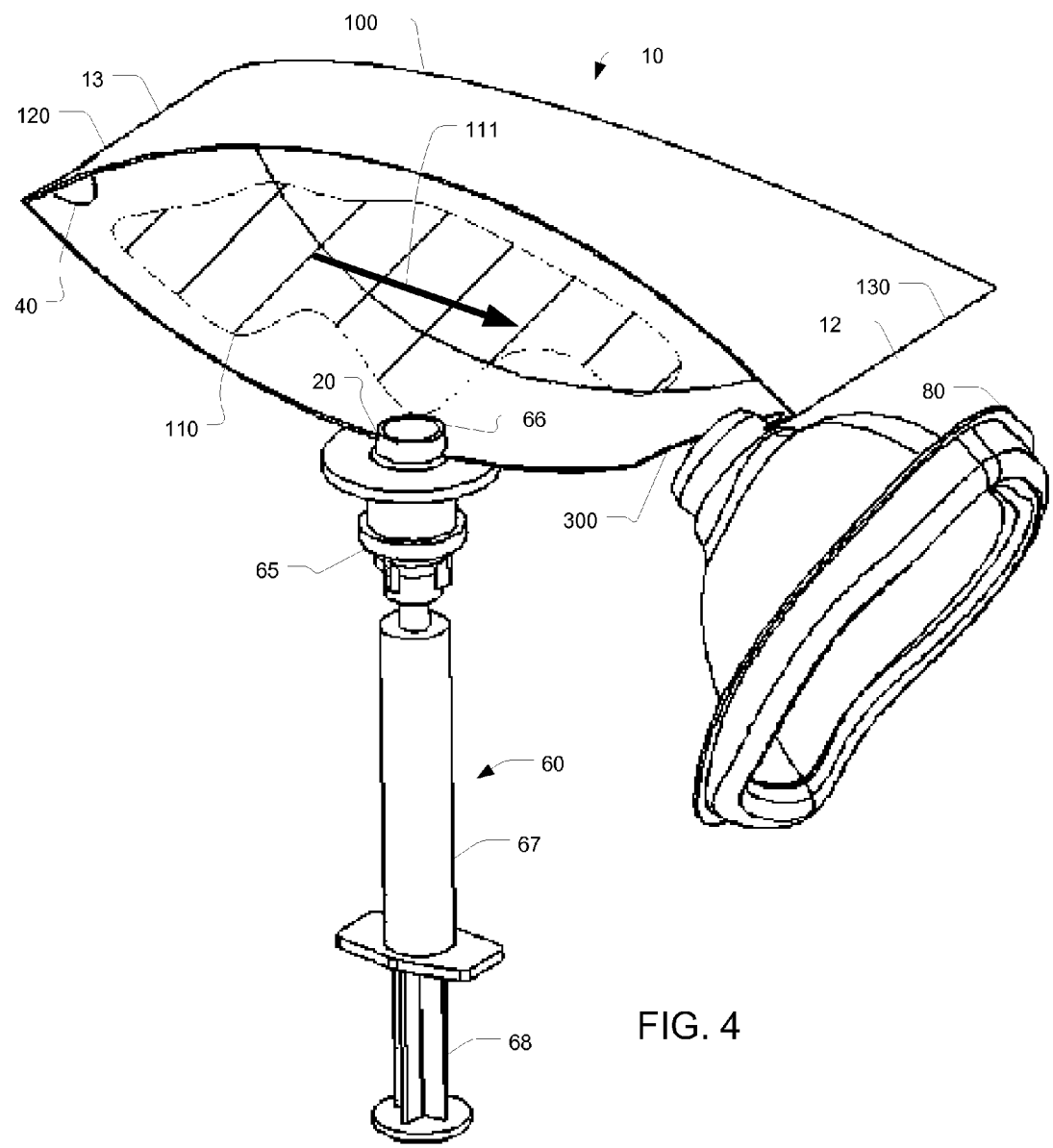
FIG. 4. shows a cut away view of the embodiment of FIG. 3.

The use of this embodiment for a second patient population (most likely a pediatric use) is shown in FIGS. 3-4 where Second end 130 becomes the distal end 12 of the device. "Distal" is defined as the portion of spacer 10 closest to the patient's face. Spacer 10 is manipulated into an expanded state. Medication delivery device 60 having capsule 65 and capsule outlet 66 is engaged to port 20 of spacer 10. Cover 350 is removed from spacer 10, and subsequently a mask 80 is engaged to orifice 300 and the patient places their mouth and/or nose substantially into mask 80. The patient and or caregiver then activates the medication delivery device 60, which in this case involves depressing plunger 68. Medicament discharged from medication delivery device 60 into spacer 10 via port 20. The vent cover 45 over outlet 40 by means of its design does not allow medication to escape. The patient then inhales and preferably outlet 40 becomes an inlet and allows the flow of air external to spacer 10 to enter the interior of spacer 10 and mix with the medicament to flow through orifice 300 and mask 80 into the patient. Preferably the patient accomplishes a full dose delivery in a single breath; however, it is not outside of the scope of the invention to perform multiple breaths utilizing the spacer. FIG. 4. shows a cut away view of the embodiment of FIG. 3 with medication plume 110 and arrow 111 represents the general direction of the airflow during inhalation. In each of these uses it is preferred to remove the covers (45, 350) at the distal end of the device prior to inhalation.

Figure 5:
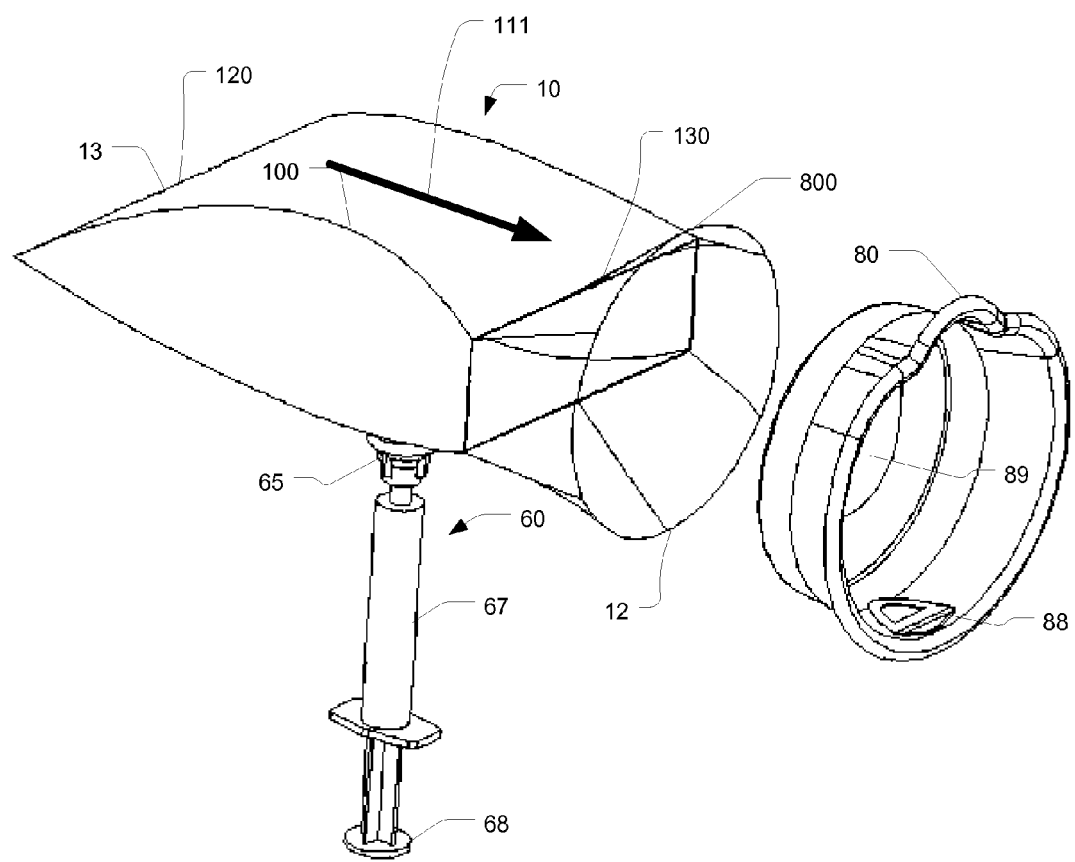
FIG. 5 shows a perspective view of an alternate embodiment of the design of FIG. 3.
Figure 6:
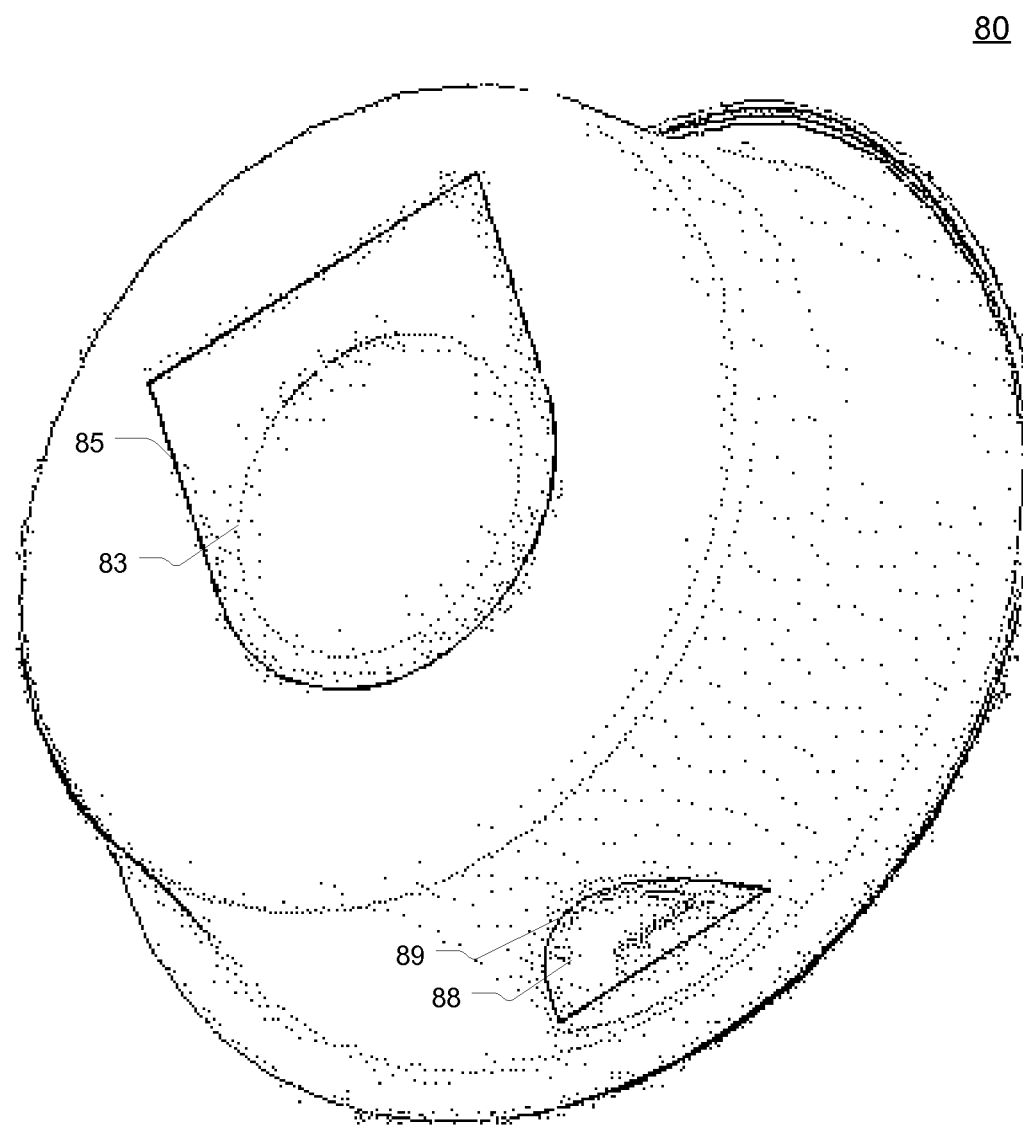
FIG. 6 shows a perspective view of the mask of the design of FIG. 5.

FIG. 5 shows a perspective view of an alternate embodiment of the design of FIG. 3, where the second end 130 of the device includes a foldable mask 800. Foldable Mask 800 is integrated into spacer 800. Spacer 10 may be used with foldable mask 800 alone, as described above in FIGS. 3-4, as a replacement for mask 80. Alternatively, foldable mask 800 serves as an interface for mask 80, as shown in FIG. 5. This embodiment of mask 80 is detailed in FIG. 6, showing optional valves 89 and 85, which integrate with mask outlet 88 and mask inlet 83, respectively, to form a valving system which enables multiple breaths to be taken using the device. Both valves (89, 85) are optional and one, none or both may be present in the mask. In a preferred embodiment of this mask, mask 80 is formed from a thermoplastic material; however it would be possible to use other materials (e.g. paper). In a preferred embodiment, these valves (89, 85) are reed valves formed from thermoplastic material (e.g. plastic film); however it would be possible to use other materials. It is envisioned that mask 80 could be either re-used or disposable. A mask is only one form of inhalation aid which is useful with the spacer. Other inhalation aids inter alia ventilator, nebulizer, diffusion tube could be used with the spacer.

Figure 7:
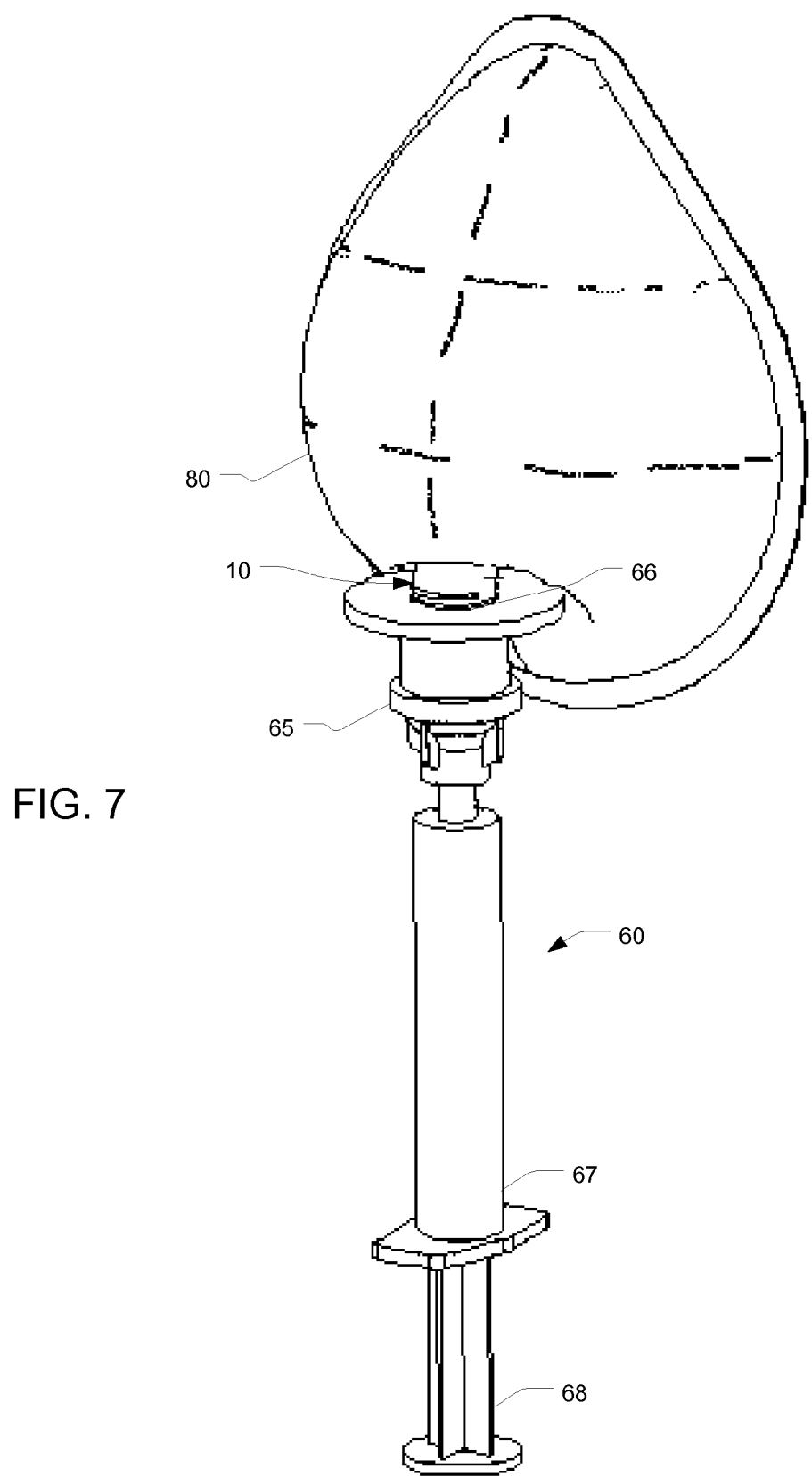
FIG. 7 shows a perspective view of an alternate embodiment having aspects of the invention utilizing a minimum volume spacer.

FIG. 7 shows an alternate embodiment having aspects of the invention utilizing a minimum volume spacer. In this embodiment, spacer 10 is designed to house a minimum volume in which medication may aerosolize at expelled from device 60. This embodiment of spacer 10 may be useful for very low dose medicament delivery, as in these low doses the volume required for aerosolization is small. Spacer 10 of this embodiment preferably includes internal diffusion features which may aid in dispersion of medicament prior to inhalation. Spacer 10 is shown engaged to mask 80 for use with one patient population; however, in this embodiment spacer 10 could be utilized without mask 80 for a second patient population.

Figure 8:
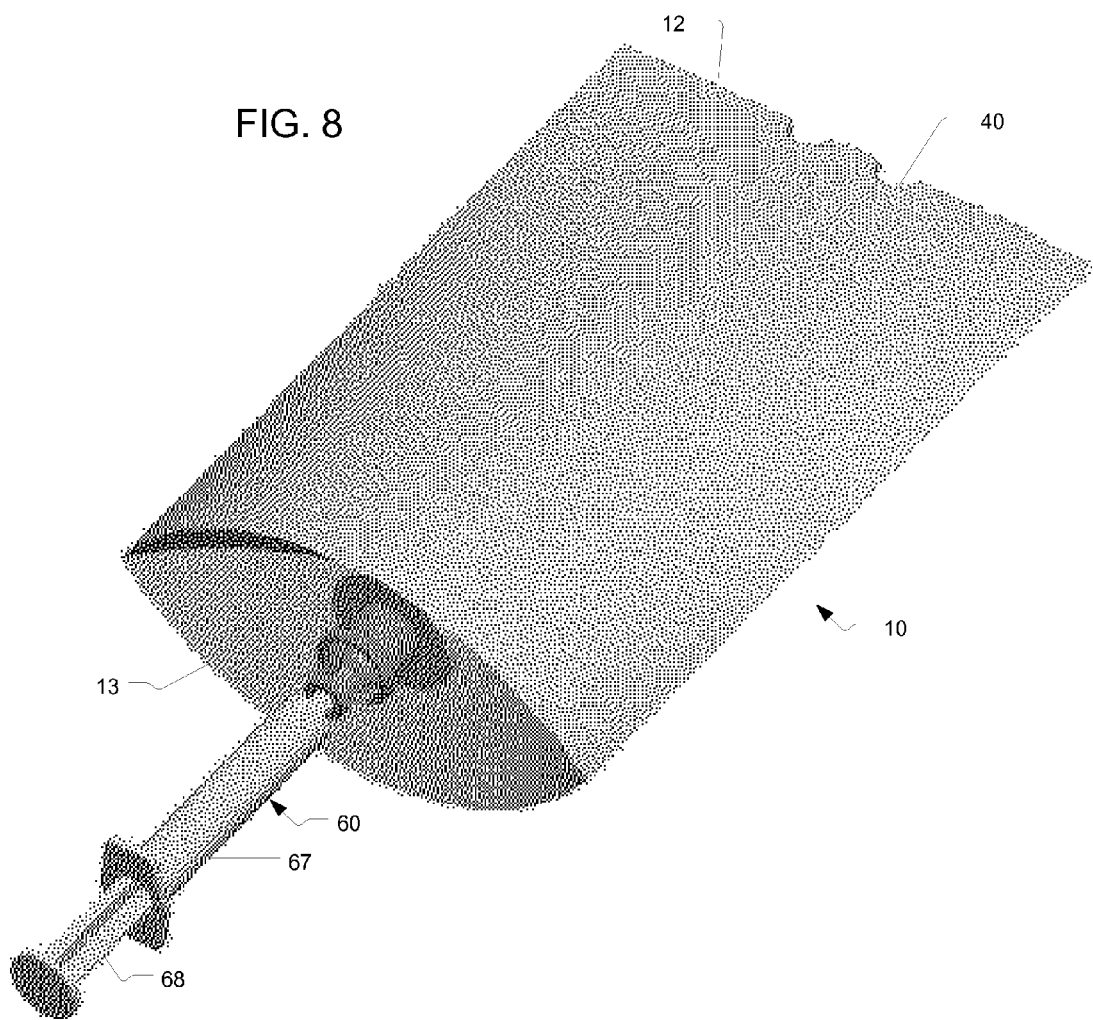
FIG. 8 shows a perspective view of an alternate embodiment having aspects of the invention utilizing an axial flow path.
Figure 11:
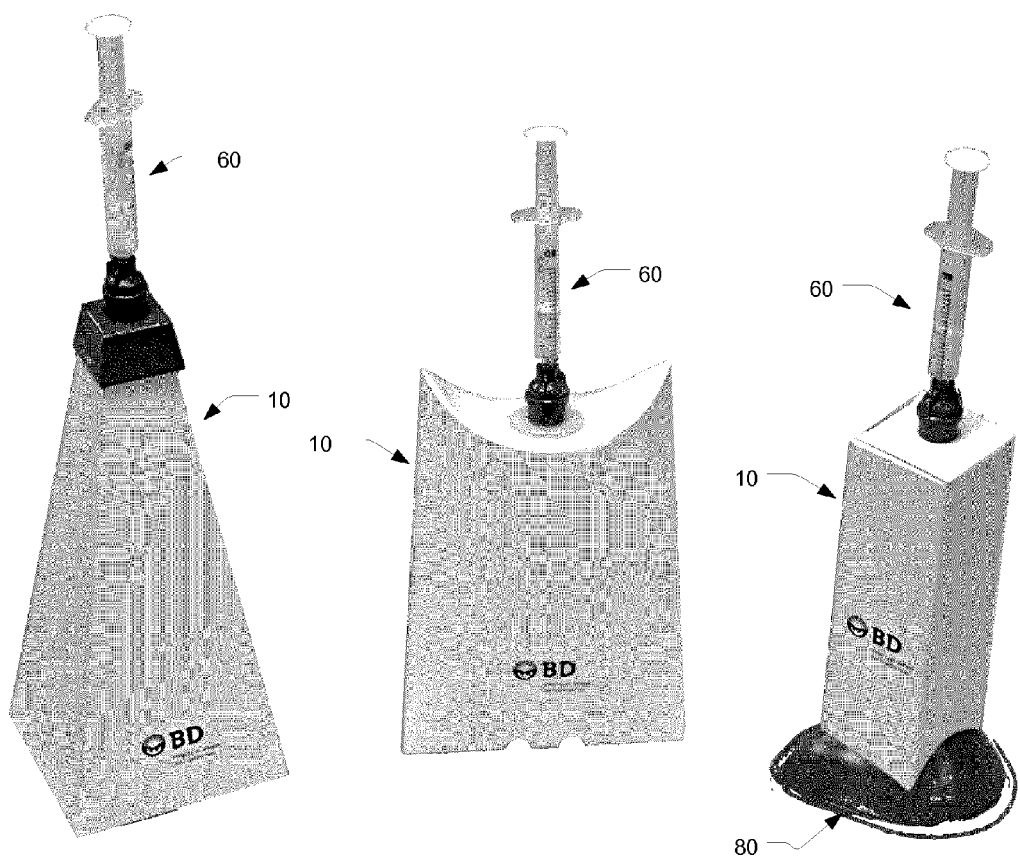
FIG. 11 shows a perspective view of three alternate embodiments having aspects of the invention utilizing an axial flow path.
Figure 12A:
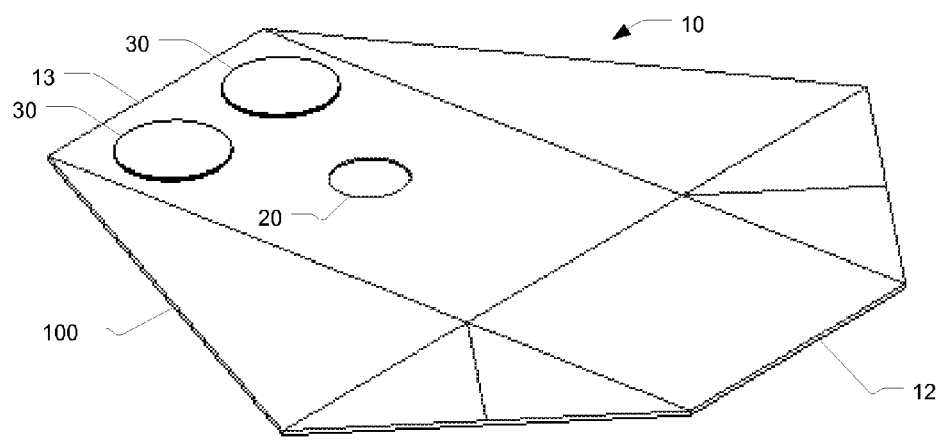
FIG. 12A shows a perspective view of an alternate embodiment having aspects of the invention in a flattened state.
Figure 12B:
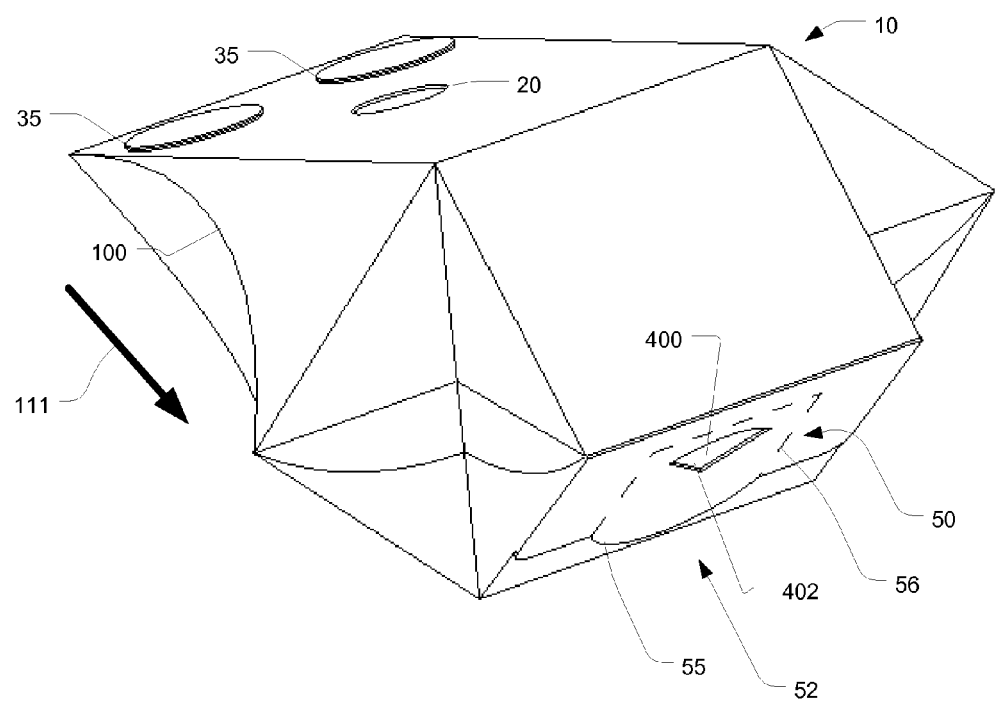
FIG. 12B shows the embodiment of 12A in an expanded state.

FIGS. 8 and 11 show alternate embodiments having aspects of the invention utilizing an axial flow path, where port 20 is placed on a side of the device rather than the top or bottom. Of course these designs could be used with any of the embodiments discussed herein.

Figure 9:
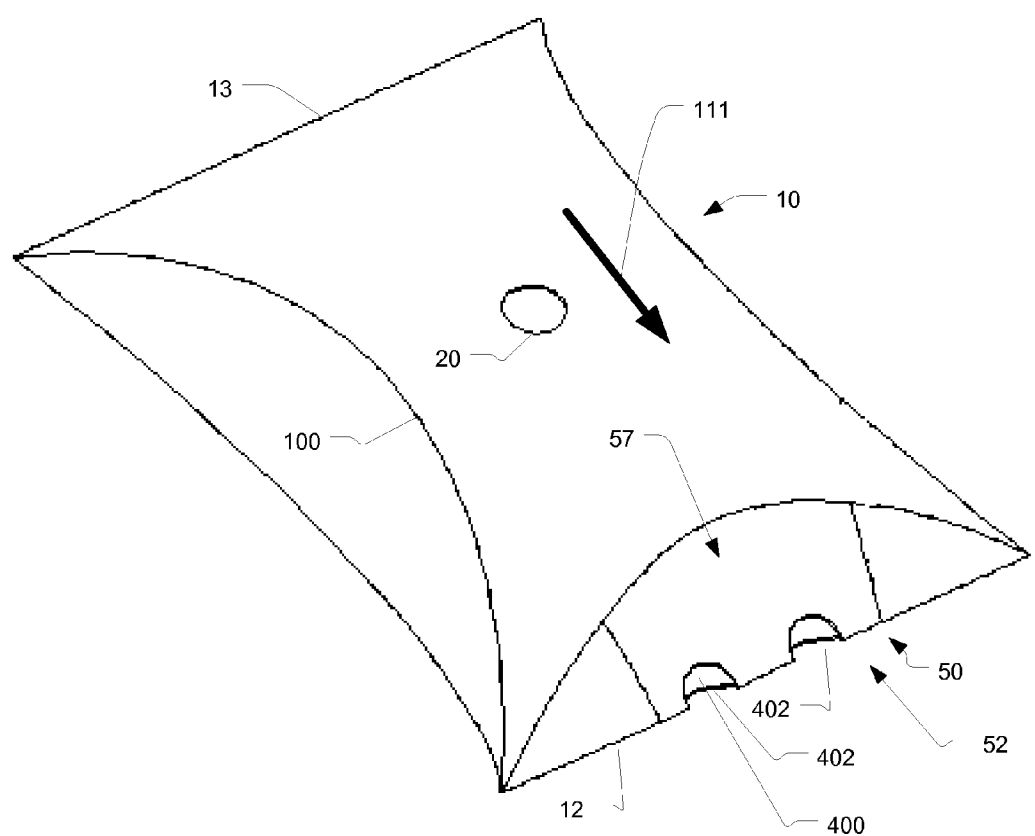
FIG. 9 shows a perspective view of an alternate embodiment having aspects of the invention utilizing a foldable outlet, in the adult mode of operation.
Figure 10:
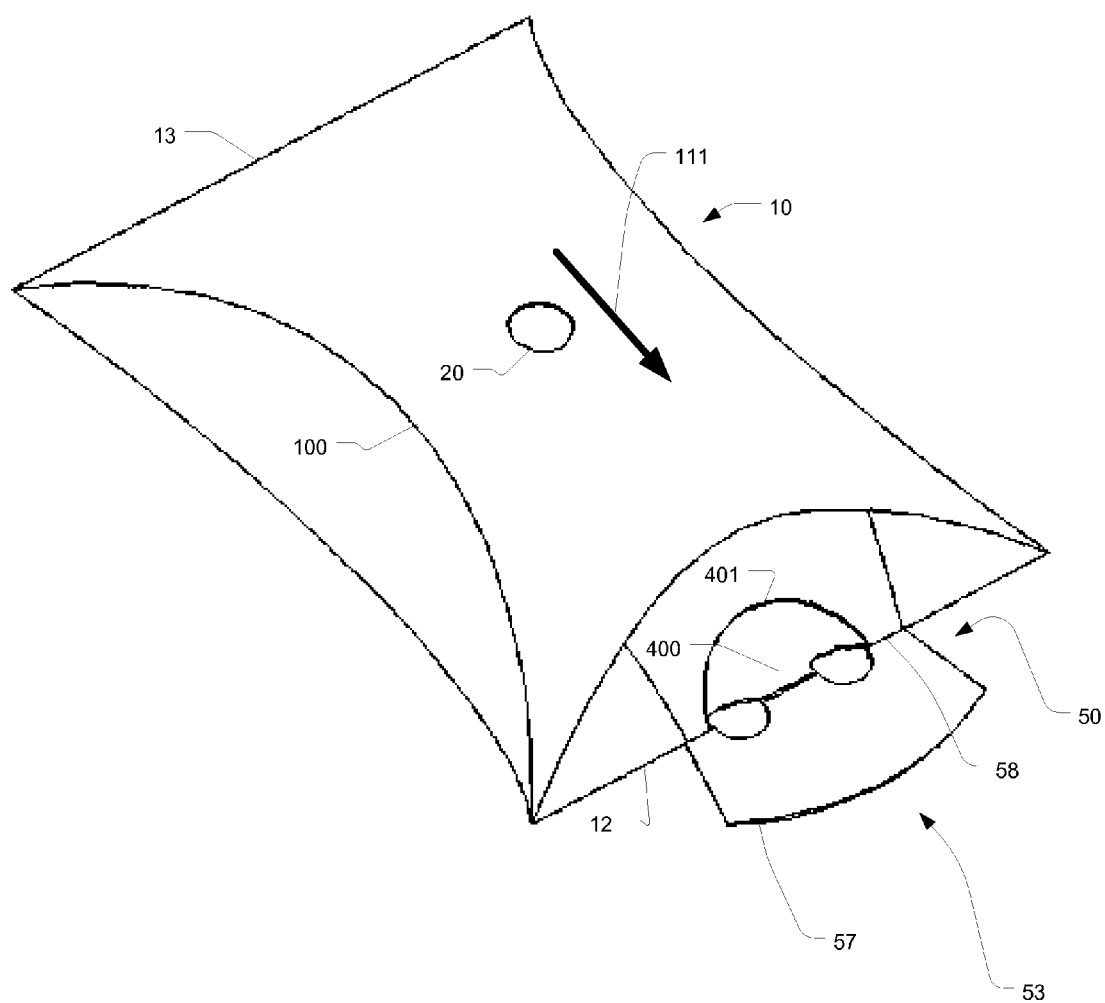
FIG. 10 shows a perspective view of the embodiment of FIG. 9, in the pediatric mode of operation.

Now turn to FIGS. 9-10, which show an alternate embodiment having aspects of the invention utilizing a foldable outlet. The operation of this device is similar to the embodiment of FIGS. 1-4, however, rather than having the multiple modes of operation at different locations (each end as in the last embodiment); the multiple modes of operation are with a single modal outlet 50. Modal outlet 50 in this embodiment is a foldable portion of spacer 10. Modal outlet has opening 400 which a first mode 52 is shown. In first mode 52 opening 400 is comprised of at least one orifice 402. Flap 57 is shown in a first position where flap 57 blocks at least a portion of opening 400 such that orifice 402 is formed. Two orifices 402 are shown in FIG. 9. Orifice(s) 402 are designed to enter the mouth, of a patient, along with a portion of distal end 12 of spacer 10, for inhalation. In this embodiment these orifices are used in an adult population. In a second mode 53 opening 400 is comprised of at least one orifice 401. Flap 57 has been folded along fold 58 to a second position where a larger portion of opening 400 is exposed to form orifice 401. Orifice (s) 401 are designed to engage a mask or other device for a second population who is unable to utilize the device using orifice(s) 402. Thus, this embodiment utilizes a single, reconfigurable outlet to serve more than one patent population with spacer 120 for inhalation of medicaments.

Now turn to FIGS. 12-18 which show an alternate embodiment having aspects of the invention utilizing a reconfigurable outlet. FIG. 12A, which shows this embodiment of the spacer 10 in flattened state having at least one inlet 30 and port 20, and structural crease 100. FIG. 12B shows spacer 10 in an expanded state, unconnected to a delivery device. Spacer 10 further includes a distal end 12, and proximal end 13. In this embodiment inlet 20 is disposed on the top surface of the spacer, however, it could be placed on the bottom surface or another surface formed when spacer 10 is expanded. The port 20 is adapted to receive a medication delivery device, preferably an inhalation medicament delivery device, more preferably a powdered medicament delivery device. Preferably inlet 20 is adapted to mate correspondingly to the medicament delivery device such that a substantially sealed connection is made between spacer 10 and the medicament delivery device.

Proximal end 13 of spacer 10 includes at least one inlet 30 covered by a corresponding inlet cover 35. This embodiment has two inlets 30; however, any number may be used. Preferably inlet 30 and inlet cover 35 allow airflow into the spacer as the patient inhales and draws the aerosolized formulation into their pulmonary tract. Inlet cover 35 is preferably a porous breathable material which limits medicament loss and is preferably attached to the spacer by a permanent peel able medical grade adhesive material. In an alternate embodiment inlet cover 35 is removable, and provides no obstruction to inlet 30. Alternatively, inlet 30 and inlet cover 35 may be located on other surfaces of spacer 10.

Figure 13A:
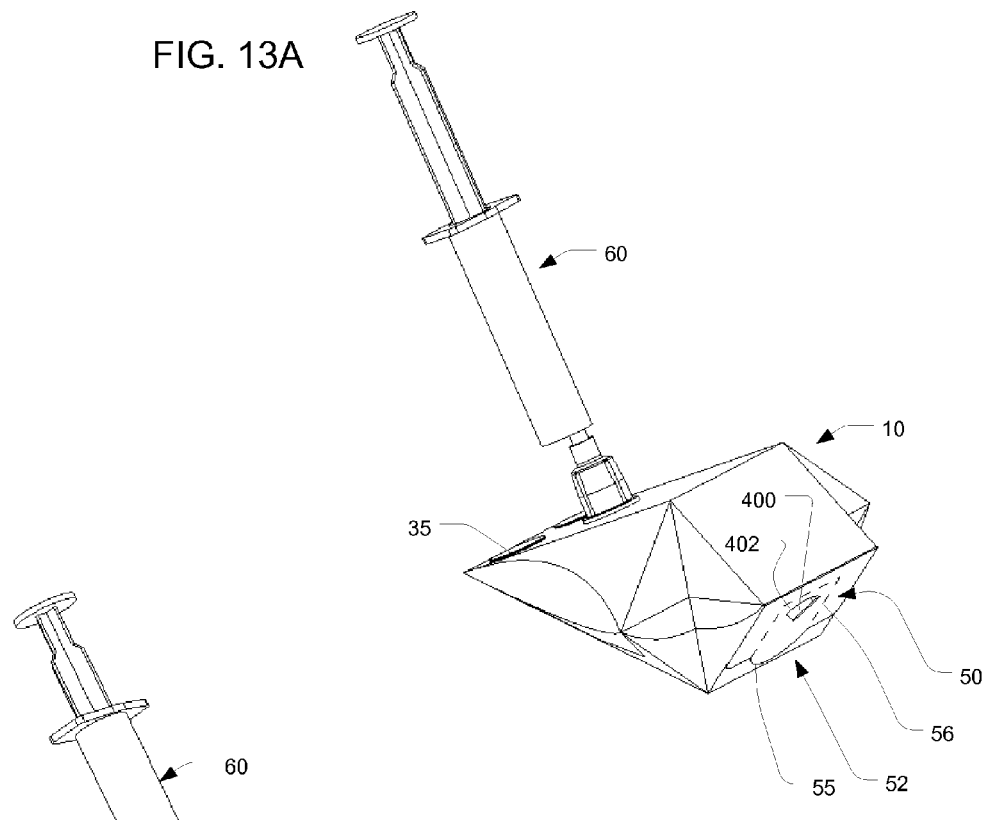
FIGS. 13A and 13B show perspective views of the adult mode and the pediatric mode, respectively, of the embodiment of FIG. 12A in an expanded state, connected to a medicament delivery device.
Figure 13B:
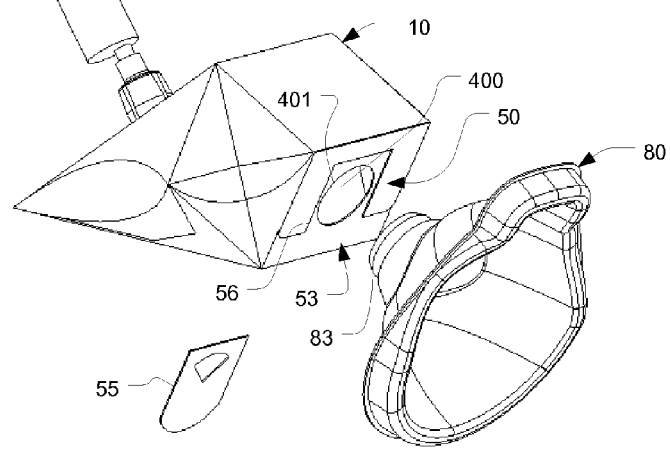

Distal end 12 of spacer 10 further includes modal outlet 50 having at least one opening 400 which is configured to be suitable for use by a first patient population. Modal outlet 50 in this embodiment is a foldable portion of spacer 10. Modal outlet has opening 400 which a first mode 52 is shown in FIG. 13A. In first mode 52 opening 400 is comprised of at least one orifice 402. Tab 55 is shown in a first position where Tab 55 blocks at least a portion of opening 400 such that orifice 402 is formed. A single orifice 402 is shown, however multiple orifices would be within the scope if the invention. Orifice 402 is designed to enter the mouth of a patient, along with a portion of distal end 12 of spacer 10, for inhalation. In this embodiment orifice 402 is used in an adult population. In FIG. 13B a second mode 53 of use of modal outlet 50 is shown. Tab 55 has been removed from spacer 10 by tearing along perforated section 56. After removal of tab 55, modal outlet 50 is in a second state where a larger portion of opening 400 is exposed to form orifice 401. Orifice 401 is designed to engage a mask inlet 83 of mask 80 or other device for a second population who is unable to utilize the device using the first mode of modal outlet 50. Thus, this embodiment utilizes a single, reconfigurable outlet to serve more than one patent population with spacer 120 for inhalation of medicaments.

Figure 14:
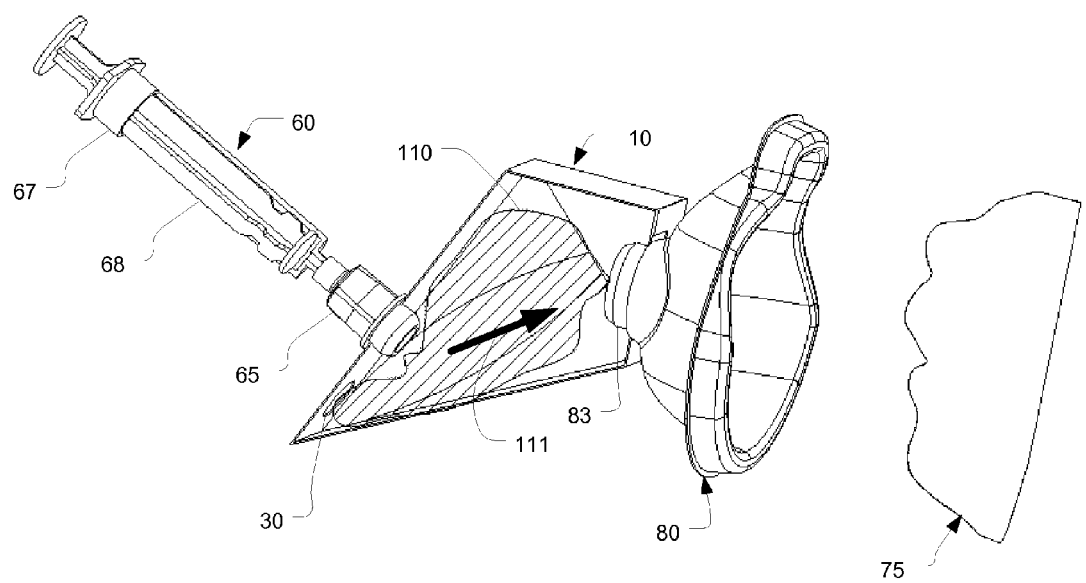
FIG. 14 shows a cut away view of the embodiment of FIG. 13B.
Figure 15:
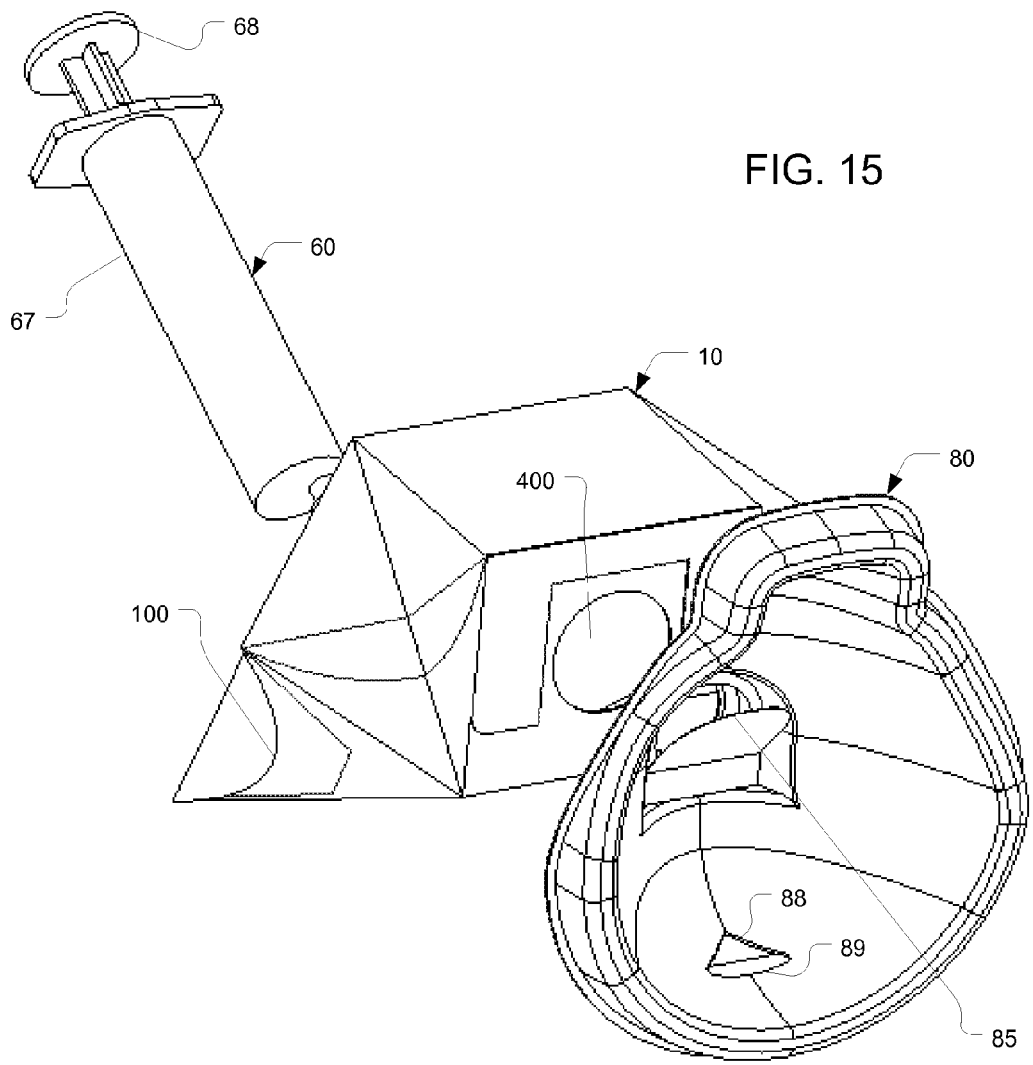
FIG. 15 shows a rotated perspective view of the embodiment of FIG. 13B.

FIG. 14 shows a cut away view of the embodiment of FIG. 13B, and from this view one can see the internal volume which has been filled with medicament 110, along with the general air flow direction represented by arrow 111 after patient 75 has engaged mask 80 and inhaled. This view also shows how mask inlet 83 is engaged to opening 400 of spacer 10 via an insert fit with detents. This view also shows how medication delivery device 60 is engaged to port 20 of spacer 10 via a press fit. Alternatively, other engagement types are possible for both connections. FIG. 15 shows a close up view of the optional valve 85.

Figure 16A:
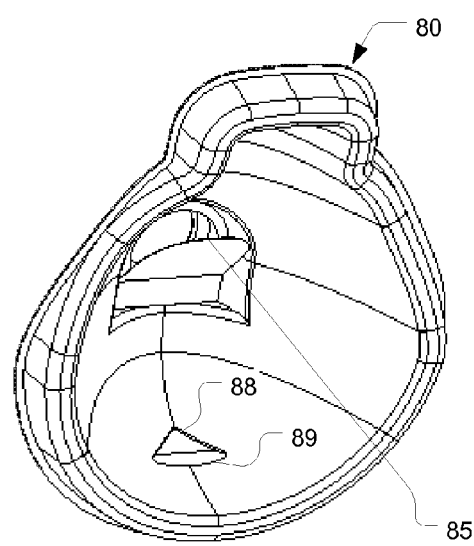
FIGS. 16A and 16B show a wireframe view of a distal perspective and proximal perspective views, respectively, of the mask of the embodiment of FIG. 13A.
Figure 16B:
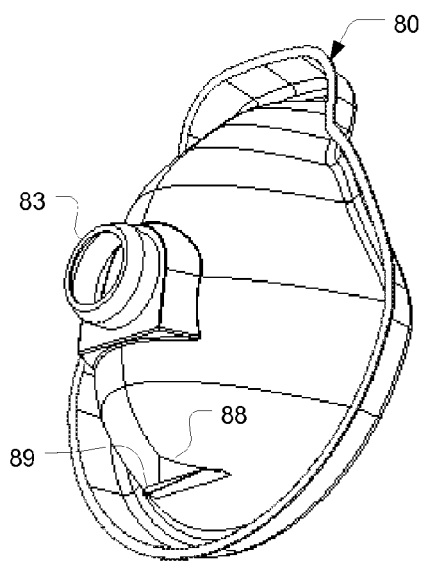
Figure 16A:
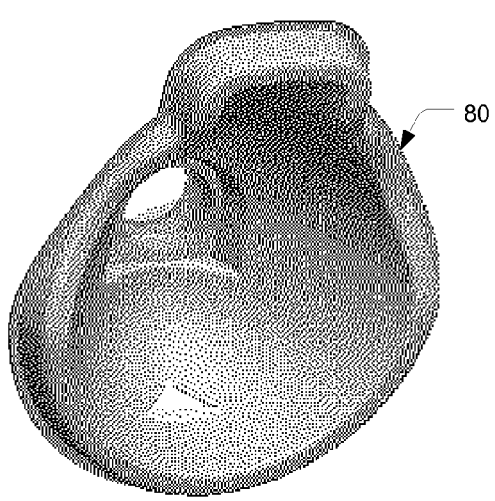
Figure 16B:
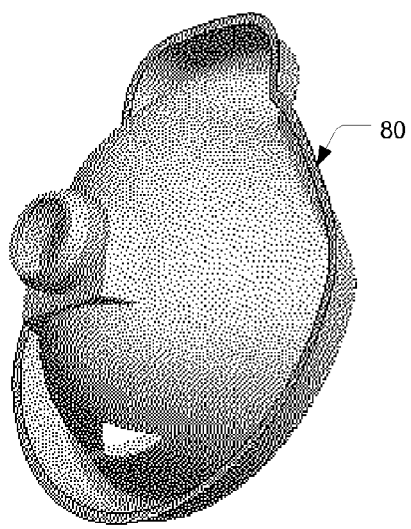

FIGS. 16A-16B' show shaded and wireframe versions of the mask 80. This embodiment of mask 80 is detailed in FIGS. 16A-16B', showing optional valves 89 and 82, which integrate with mask outlet 88 and mask inlet 83, respectively, to form a valving system which enables multiple breaths to be taken using the device. In a preferred embodiment of this mask, mask 80 is formed from a thermoplastic material; however it would be possible to use other materials (e.g. paper). In a preferred embodiment, these valves (89, 85) are reed valves formed from thermoplastic material (e.g. plastic film); however it would be possible to use other materials. It is envisioned that mask 80 could be either re-used or disposable.

Figure 17:
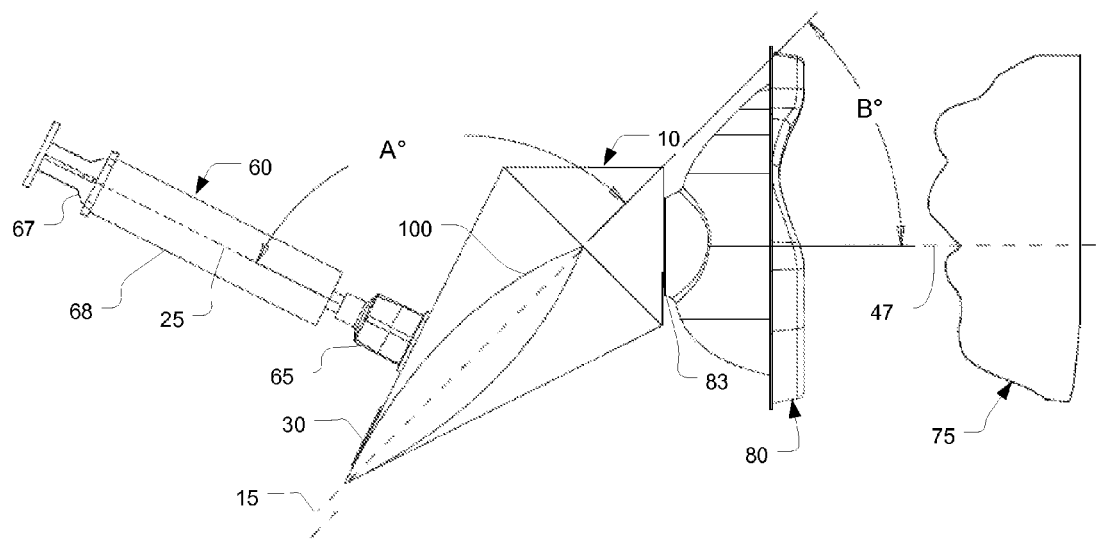
FIG. 17 shows a side view of the embodiment of FIG. 13B.

Now turn to FIG. 17 which shows a side view of the embodiment of FIG. 13B, and the geometric arrangement of the parts. This view shows port 20 on spacer 10 with a port axis 25. Port axis 25 is substantially orthogonal to the plane of the port opening, and generally corresponds to the outlet axis of the medication delivery device 60. This view shows spacer longitudinal axis 15. This view shows an outlet port axis 47. Outlet axis 47 is substantially orthogonal to the plane of the outlet 400 opening, and generally corresponds to the inlet axis of mask 80. Also shown in this figure is angular dimension "A" between the port axis 25 and the spacer longitudinal axis 15. Also shown in this figure is angular dimension "B" between the outlet axis 47 and the spacer longitudinal axis 15. Preferably dimension "A" is 108°±10° and Dimension "B" is 45°±10°. It is not likely performance would be significantly impacted outside this range. With powdered delivery device it is likely that a deviation of +45 degrees of angle "A" would still allow the device to perform properly, however, the fit between the spacer and medication delivery device the may not be airtight, but it would still work. However, decreasing angle "A" beyond the tolerances above would likely result in an emitted dose decrease.

Figure 18:
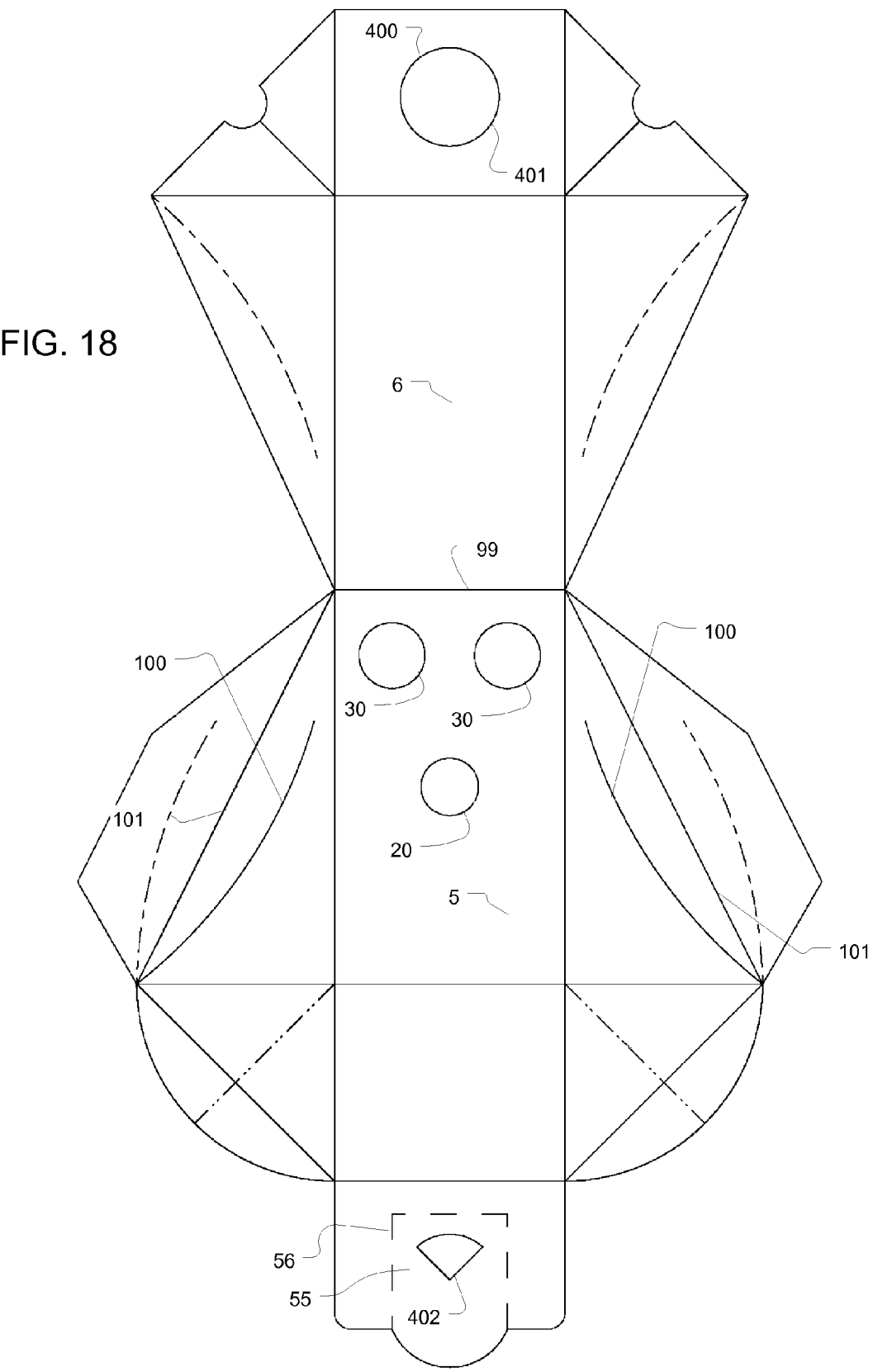
FIG. 18 shows a flattened, unfolded view of the spacer of embodiment of FIG. 13B.

Now turn to FIG. 18 which shows flattened view of the embodiment of spacer 10 in FIGS. 12-17, and the geometric arrangement of the parts. This view shows port 20 which has a diameter of approximately 0.438 inches. This view shows an opening 400 which has a diameter of approximately 0.750 inches. Inlets 30 have a diameter of approximately 0.500 inches. Spacer 10 is formed by folding the flat stock along primary fold 99 and assembling and/or gluing tabs in place.

Having described the invention in general, the following specific but not limiting examples and reference to the accompanying Figures set forth various examples for practicing the inhalation method and device and examples of inhaled drug substances providing improved effects. Both examples below utilized the embodiment of FIG. 1, however the findings may be representative of all embodiments.

EXAMPLE 1

An in-vitro study was performed comparing the delivery of a dry powder dose with a commercially available cardstock device (Liteaire®). In this experiment, the powder was dispersed from the dry powder syringe-activated device into each of the two spacers. A breathing pattern was established with a breathing simulator that controlled the tidal volume, inspiratory and expiratory rates. This respiratory pattern passed through a standard in-vitro airway model (SAINT model—H. Janssens, J Aerosol Med. 14:4 433 (2001)) This was mated with a standard Cascade Impactor to quantify the amount of powder that could be delivered to the lungs, thus measuring emitted dose. This was repeated three times. Breathing rate was set at 30 times per minute in the ratio of 1:1.3 inspiration: expiration and the tidal volume was 100 ml, nominally that of a healthy two year old. The delivery time was 30 seconds and started with an inspiration. Since the same device was used to disperse the powder in both cases, the emitted dose was confirmed to be the same. By way of comparison, the particles are classified by size and the mass in each range is measured:

The following data represents improvements of a device having aspects of the invention over the Liteaire® Device:

Lung Dose (particles that were less than 9 microns) +47%

Fine Particle Fraction (particles that were less than 4.7 microns) +43%

Extra fine particle fraction (particles that were less than 2.1 microns) +28%

This improvement is anticipated to correlate with improved efficacy of a device having aspects of the invention in pulmonary delivery.

EXAMPLE 2

Using the same equipment configuration, a study was performed to evaluate the impact of breathing coordination with actuation of the device. In this test, actuation of the device either occurred as the model breathed in or as the model breathed out. Typically in adults this breathing coordination can be taught but can not be easily accomplished in young children. In this case we compare the improvement in lung dose (particles that were less than 9 microns) as a result of the invention:

|  | Present invention | Lite Aire ® Spacer | Improvement |
|---|---|---|---|
| Inhale | 9.5 | 1.0 | 9X |
| Exhale | 7.1 | 1.8 | 4X |

Thus, aspects of the invention described here provide a disposable chamber which allow for natural inhalation and exhalation by the patient. In some embodiments, the device can be maintained in a collapsed, flat configuration, suitable for bulk storage in a minimum space, and expanded immediately prior to use, after which it can be discarded or re-folded for later use by the same patient. In other embodiments, a multi mode reconfigurable outlet is provided which serves multiple patient populations. The described chamber is ideal for use for a plurality of patient populations and has features adapted for more than one population. Aspects of the invention are well suited for use in mass immunization. In addition, the portability and low cost of a device having aspects of the invention make it ideal for use by relief or world health organizations, especially for aerosol vaccines.

Although the foregoing invention has been described in some detail by way of illustration and example for purposes of clarity of understanding, it will be obvious that certain changes and modifications may be practiced within the scope of the appended claims.

That which is claimed:

1. A spacer for a medicament inhalation delivery device for delivery of medication to a patient, comprising:
   a body having opposed ends; a passage having and a volume extending through said body through said opposed ends;
   an inlet port for connection to the inhalation delivery device in fluid communication with the passage;
   an intake port for aspiration of air external to the passage in fluid communication to the passage;
   a plurality of reconfigurable outlets in fluid communication with the passage which allows use of the spacer for at least two patient populations; wherein a first outlet is located at one end of the body adapted to treat a first patent population; and a second outlet is located at the opposed end of the body adapted to treat a second patent population;
   wherein one of the unused reconfigurable outlets acts as said intake port.

2. The spacer of claim 1, wherein the body is comprised of an expandable structure having a first state wherein the volume of the passage is maximized and a second state wherein the volume of the passage is minimized.

3. The spacer of claim 1, wherein the first outlet is adapted for direct use by the patient and the second outlet is adapted for use with an inhalation aid.

4. The spacer of claim 3, wherein the inhalation aid is a mask adapted to fit over both a patient's mouth and a patient's nose.

5. The spacer of claim 4, wherein the mask further comprises a mask inlet which is in fluid communication with the spacer second outlet, wherein the mask inlet further comprises a one-way mask inlet valve which substantially prevents flow from the mask to the spacer.

6. The spacer of claim 4, wherein the mask further comprises a mask outlet adapted to vent to the atmosphere, wherein the mask outlet further comprises a one-way mask outlet valve which substantially prevents flow directly from the atmosphere to the mask.

7. The spacer of claim 5, wherein the mask further comprises a mask outlet adapted to vent to the atmosphere, wherein the mask outlet further comprises a one-way mask outlet valve which substantially prevents flow directly from the atmosphere to the mask.

8. The spacer of claim 1, wherein at least one reconfigurable outlet of the plurality of reconfigurable outlets is a single opening in fluid communication to the passage further comprising:
   a first mode wherein a portion of the reconfigurable outlet is occluded and the first mode allows direct use of the spacer by the patient; and
   a second mode wherein the reconfigurable outlet is substantially open and is adapted for use with an inhalation aid.

9. The spacer of claim 8, wherein the body is comprised of an expandable structure having a first state wherein the volume of the passage is maximized and a second state wherein the volume of the passage is minimized.

10. The spacer of claim 9, wherein the body is comprised substantially of folded and creased paper stock.

11. The spacer of claim 8, wherein the inhalation aid is a mask adapted to fit over both a patient's mouth and a patient's nose.

12. The spacer of claim 11, wherein the mask further comprises a mask inlet which is in fluid communication with the single opening, wherein the mask inlet further comprises a one-way mask inlet valve which substantially prevents flow from the mask to the spacer.

13. The spacer of claim 11, wherein the mask further comprises a mask outlet adapted to vent to the atmosphere, wherein the mask outlet further comprises a one-way mask outlet valve which substantially prevents flow directly from the atmosphere to the mask.

14. The spacer of claim 12, wherein the mask further comprises a mask outlet adapted to vent to the atmosphere, wherein the mask outlet further comprises a one-way mask outlet valve which substantially prevents flow directly from the atmosphere to the mask.

* * * * *

UNITED STATES PATENT AND TRADEMARK OFFICE
CERTIFICATE OF CORRECTION

PATENT NO.        : 8,413,651 B2                                    Page 1 of 1
APPLICATION NO.   : 12/593731
DATED             : April 9, 2013
INVENTOR(S)       : Powell et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 745 days.

Signed and Sealed this

First Day of September, 2015

Michelle K. Lee
*Director of the United States Patent and Trademark Office*